(12) United States Patent
Stad et al.

(10) Patent No.: US 10,765,466 B2
(45) Date of Patent: Sep. 8, 2020

(54) BONE ANCHOR DRIVER AND METHODS

(71) Applicant: Medos International Sarl, Le Locle (CH)

(72) Inventors: Shawn Stad, Lakeville, MA (US); Nils Schmuckli, Dissach (CH)

(73) Assignee: Medos International Sarl, Le Locle (CH)

( * ) Notice: Subject to any disclaimer, the term of this patent is extended or adjusted under 35 U.S.C. 154(b) by 213 days.

(21) Appl. No.: 15/972,654

(22) Filed: May 7, 2018

(65) Prior Publication Data

US 2018/0256234 A1 Sep. 13, 2018

Related U.S. Application Data

(62) Division of application No. 14/570,559, filed on Dec. 15, 2014, now Pat. No. 9,987,066.

(51) Int. Cl.
*A61B 17/88* (2006.01)
*A61B 17/70* (2006.01)
*A61B 90/00* (2016.01)

(52) U.S. Cl.
CPC ...... *A61B 17/8886* (2013.01); *A61B 17/7091* (2013.01); *A61B 17/8894* (2013.01); *A61B 17/7032* (2013.01); *A61B 2090/031* (2016.02)

(58) Field of Classification Search
CPC .................................. A61B 17/7074–17/7091
See application file for complete search history.

(56) References Cited

U.S. PATENT DOCUMENTS

| | | | | |
|---|---|---|---|---|
| 4,721,169 A | * | 1/1988 | Nagasawa | B25B 23/14 173/178 |
| 5,531,461 A | * | 7/1996 | Huff | B23B 31/1238 279/140 |
| 6,640,674 B1 | * | 11/2003 | Rinner | B25B 23/141 81/473 |
| 6,755,829 B1 | | 6/2004 | Bono et al. | |
| 7,073,415 B2 | | 7/2006 | Casutt et al. | |
| 7,243,581 B1 | * | 7/2007 | Gao | B25B 23/141 192/38 |
| 7,272,998 B1 | * | 9/2007 | Gauthier | B25B 23/141 81/473 |

(Continued)

FOREIGN PATENT DOCUMENTS

| | | | | |
|---|---|---|---|---|
| CA | 2886636 A1 | * | 4/2014 | ......... A61B 17/7032 |
| WO | 2009060389 A1 | | 5/2009 | |
| WO | WO-2009060389 A1 | * | 5/2009 | ......... A61B 17/7076 |

*Primary Examiner* — Zade Coley
(74) *Attorney, Agent, or Firm* — Mintz Levin Cohn Ferris Glovsky and Popeo, P.C.

(57) ABSTRACT

Methods and devices are provided for using a bone anchor driver for driving inner and outer set closure mechanisms or set screws into a bone anchor assembly. In one embodiment, a bone anchor driver is provided that includes an outer shaft configured to engage an outer set screw coupled to a bone anchor assembly, an inner shaft disposed within the outer shaft and configured to engage an inner set screw coupled to the bone anchor assembly, and a torque limiting mechanism configured to automatically switch between a first position in which it is disengaged from the inner shaft and is engaged with the outer shaft, and a second position in which it is disengaged from the outer shaft and is engaged with the inner shaft.

19 Claims, 9 Drawing Sheets

(56) References Cited

U.S. PATENT DOCUMENTS

| | | | |
|---|---|---|---|
| 7,992,472 B2 * | 8/2011 | Gao | B25B 15/02 |
| | | | 81/475 |
| 8,007,522 B2 * | 8/2011 | Hutchinson | A61B 17/88 |
| | | | 606/279 |
| 8,105,328 B2 * | 1/2012 | Protopsaltis | A61B 17/7091 |
| | | | 606/104 |
| 8,152,810 B2 * | 4/2012 | Jackson | A61B 17/7037 |
| | | | 606/86 A |
| 8,172,847 B2 * | 5/2012 | Dziedzic | A61B 17/7091 |
| | | | 606/86 A |
| 8,206,394 B2 * | 6/2012 | Stad | A61B 17/7091 |
| | | | 606/86 A |
| 8,241,288 B2 | 8/2012 | Justin et al. | |
| 8,313,516 B2 | 11/2012 | Konieczynski et al. | |
| 8,475,466 B2 * | 7/2013 | Chenaux | A61B 17/8875 |
| | | | 606/104 |
| 8,512,381 B2 | 8/2013 | Bergeron et al. | |
| 8,876,869 B1 * | 11/2014 | Schafer | A61B 17/7032 |
| | | | 606/278 |
| 2004/0158247 A1 * | 8/2004 | Sitiso | A61B 17/7032 |
| | | | 606/914 |
| 2008/0119862 A1 | 5/2008 | Wicker et al. | |
| 2009/0264893 A1 * | 10/2009 | Beale | A61B 17/7091 |
| | | | 606/99 |
| 2010/0212460 A1 | 8/2010 | Buss et al. | |
| 2010/0292742 A1 * | 11/2010 | Stad | A61B 17/7091 |
| | | | 606/86 A |
| 2011/0066156 A1 * | 3/2011 | McGahan | A61B 17/7091 |
| | | | 606/99 |
| 2011/0245833 A1 | 10/2011 | Anderson | |
| 2012/0022594 A1 | 1/2012 | Walker et al. | |
| 2012/0274253 A1 | 11/2012 | Fair et al. | |
| 2013/0066386 A1 | 3/2013 | Biedermann et al. | |
| 2014/0094849 A1 * | 4/2014 | Spratt | A61B 17/7035 |
| | | | 606/257 |
| 2014/0277159 A1 | 9/2014 | Spratt et al. | |
| 2016/0166360 A1 | 6/2016 | Stad et al. | |

* cited by examiner

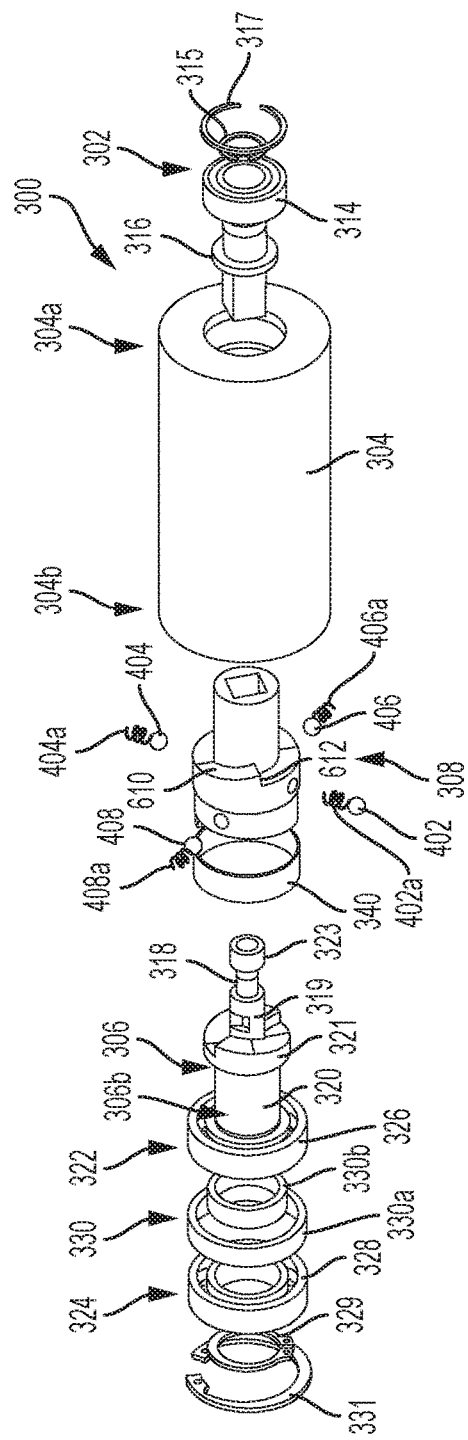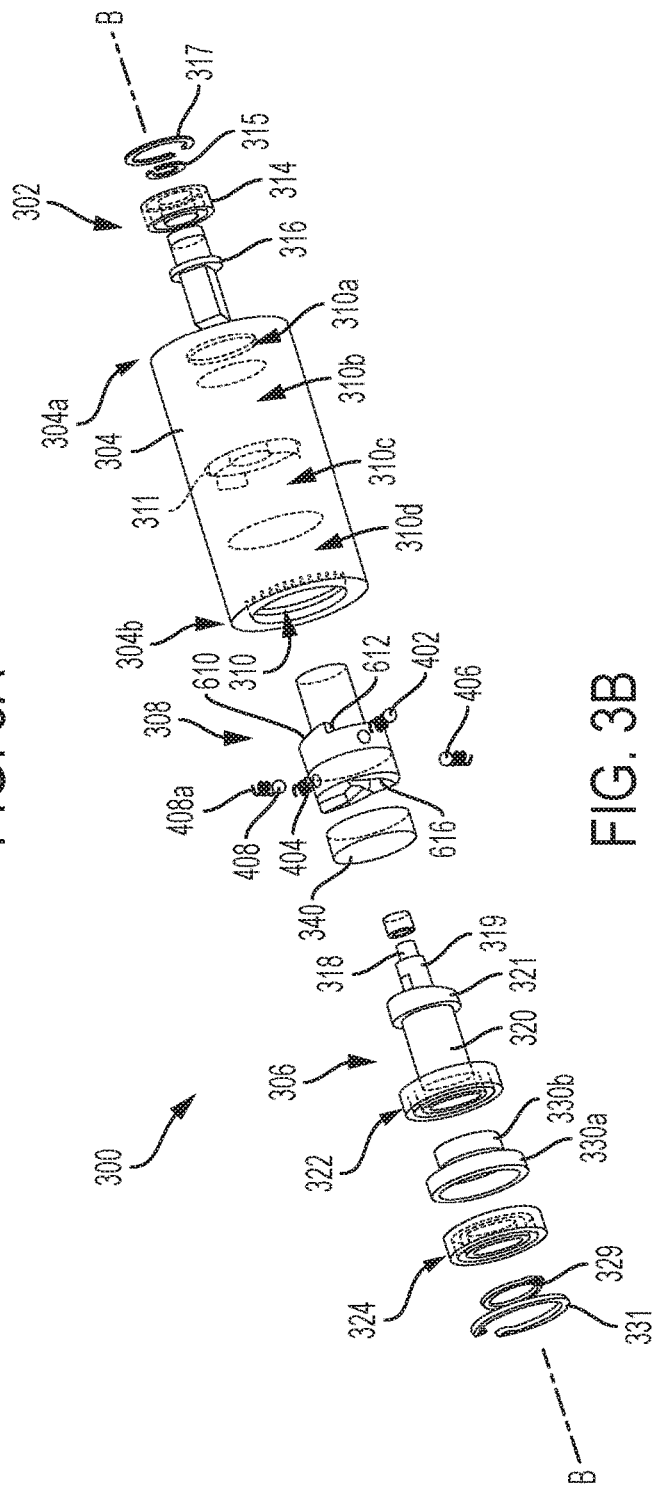

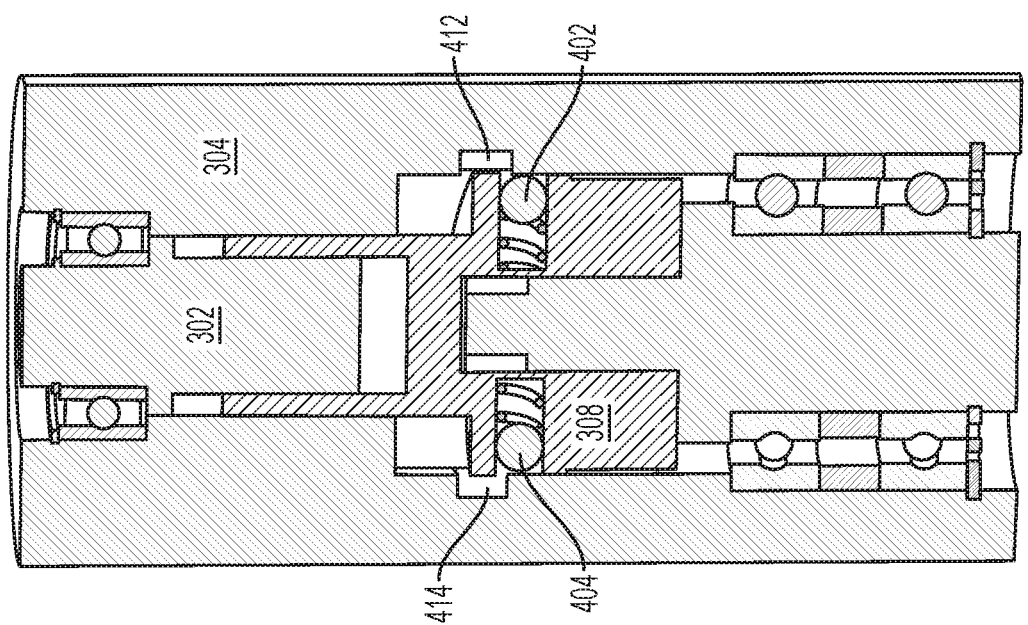
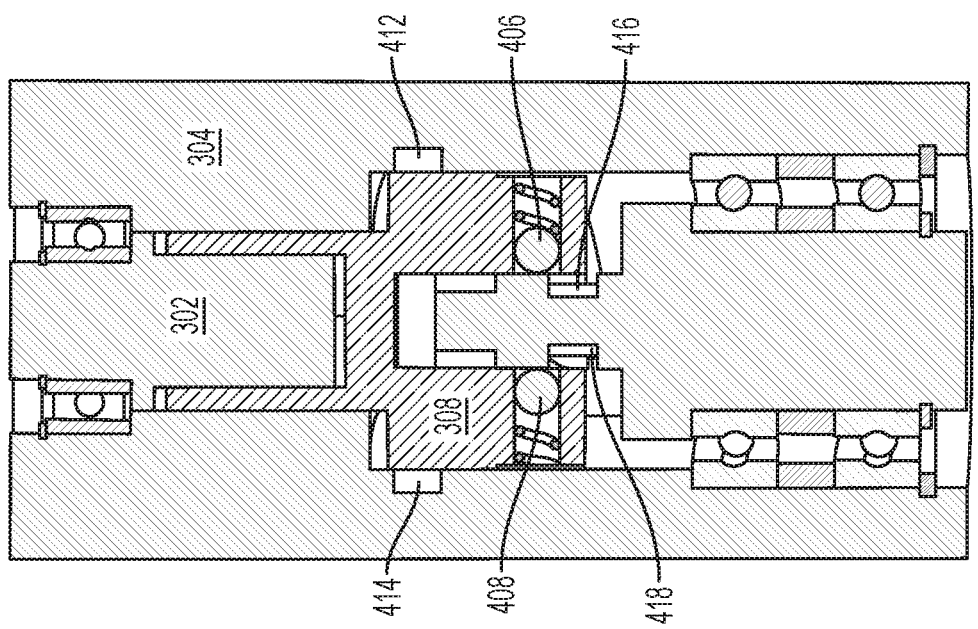
FIG. 4C
FIG. 4D

BONE ANCHOR DRIVER AND METHODS

CROSS-REFERENCE TO RELATED APPLICATIONS

This application is a divisional of, and claims priority to, U.S. patent application Ser. No. 14/570,559, filed Dec. 15, 2014, and entitled BONE ANCHOR DRIVER AND METHODS, the entirety of which is incorporated herein by reference.

FIELD OF THE INVENTION

Methods and devices are provided for applying a closure device to a bone anchor.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod or plate that is coupled to adjacent vertebrae by attaching the element to various anchoring devices, such as hooks, bolts, wires, or screws. The fixation elements can have a predetermined contour that has been designed according to the properties of the target implantation site, and once installed, the fixation element holds the vertebrae in a desired spatial relationship, either until desired healing or spinal fusion has taken place, or for some longer period of time.

Spinal rods can be mated to a number of anchoring devices fixed to or engaged with the vertebrae along a segment of the spinal column. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element. A set screw, a plug, or other fastening elements can be used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other closure mechanism to securely interconnect each screw and the fixation rod.

The process of placing a rod within or adjacent to an implanted bone anchor so that they are interconnected is referred to as "reducing" the rod. Rod reduction is typically performed using suitable instruments that can create appropriate forces on the implanted bone anchor and the rod. Furthermore, after the rod is seated in the rod-receiving member and captured in a rod-receiving portion of the head of a bone anchor (e.g., a pedicle screw), a final tightening is typically performed on the screw using fastening instruments, for stabilization of the rod. The tightening of the screw can also be performed for maintenance of a surgical correction.

To complete rod reduction and perform final tightening, surgeons use multiple instruments (e.g., screw drivers and torque wrenches) which often need to be applied in multiple steps. This can be a time-consuming and complicated procedure, particularly when multiple bone anchors are used to fixate a rod and/or when the surgical procedure is performed to correct a complex deformity or injury. Multiple steps that require application of manual force induce fatigue so that surgeon's performance during surgery can decrease, which can compromise the outcome of the surgery. As another drawback of existing approaches, torque created by the instruments during the final tightening can be difficult to control.

Accordingly, there is a need for improved methods and devices for applying a closure device to a spinal anchoring device.

SUMMARY OF THE INVENTION

Methods and devices are provided for applying a closure mechanism to a spinal anchor. In general, a bone anchor driver is provided that is configured to drive a first closure mechanism into a bone anchor, and that has a torque limiting mechanism that causes the driver to automatically switch to drive a second closure mechanism into the bone anchor.

In one aspect, a bone anchor driver for driving inner and outer closure mechanisms onto a bone anchor assembly is provided. In some embodiments, the bone anchor driver includes an outer shaft configured to engage an outer closure mechanism coupled to a bone anchor assembly, and an inner shaft disposed within the outer shaft and configured to engage an inner closure mechanism coupled to a bone anchor assembly. In one embodiment, the bone anchor driver can be used to couple the inner closure mechanism with the bone anchor assembly. In such an embodiment, the closure mechanism is not in contact with the bone anchor assembly prior to operation of the bone anchor driver.

The bone anchor driver further includes a torque limiting mechanism configured to automatically switch between a first position in which the torque limiting mechanism is disengaged from the inner shaft and is engaged with the outer shaft, and a second position in which the torque limiting mechanism is disengaged from the outer shaft and is engaged with the inner shaft. The bone anchor driver can also include an actuator configured to apply a rotational force to the torque limiting mechanism to selectively drive the inner and outer shafts.

The torque limiting mechanism of the bone anchor driver, which can be disposed between the inner and outer shafts, can vary in a number of ways. In one embodiment, the torque limiting mechanism can be configured to switch between the first and second positions when a torque applied to the torque limiting mechanism exceeds a threshold torque. In one embodiment, the inner and outer shafts can define a longitudinal axis, and the torque limiting mechanism can translate axially along the longitudinal axis to move between the first and second positions.

In one embodiment, at least one of the inner and outer shafts includes a ramp that causes the torque limiting mechanism to translate axially when the torque limiting mechanism moves between the first and second positions.

The torque limiting mechanism can include a first engaging member configured to engage with a first complementary engaging member of the outer shaft and a second engaging member configured to engage with a second complementary engaging member of the inner shaft.

The first and second engaging members can vary in a number of ways. For example, the first engaging member can be positioned in a first plane and the second engaging member can be positioned in a second plane that is spaced a distance apart from the first plane. The first engaging member and the first complementary engaging member can be positioned in the same plane when the torque limiting mechanism is in the first position, and the first engaging member and the first complementary engaging member can be positioned in different planes when the torque limiting mechanism is in the second position.

In one embodiment, the first engaging member can be disposed within a first bore extending through the torque limiting mechanism, and the second engaging member can be disposed within a second bore extending through the torque limiting mechanism. The first and second bores can vary in a number of ways. For example, an axis of the first bore can extend transverse to an axis of the second bore.

In one embodiment, the torque limiting mechanism can be in the first position when a torque applied thereto is less than or equal to a threshold torque and the first engaging member is biased into engagement with the first complementary engaging member so that the torque limiting mechanism is disengaged from the inner shaft and is engaged with the outer shaft to drive the outer shaft. When the torque exceeds the threshold torque, the first engaging member can be configured to disengage from the first complementary engaging member and to switch from the first position to the second position in which the second engaging member is biased into engagement with the second complementary engaging member in the inner shaft so that the torque limiting mechanism is disengaged from the outer shaft and is engaged with the inner shaft to drive the inner shaft.

In another aspect, a bone anchor and driver assembly is provided that includes a bone screw and a bone anchor driver. The bone anchor can have a bone engaging member configured to be implanted in bone, a receiver member polyaxially coupled to the bone engaging member and configured to receive a spinal fixation element therein, an outer closure mechanism configured to mate to the receiver member for locking a polyaxial position of the receiver member with respect to the bone engaging member, and an inner closure mechanism configured to be received within the outer closure mechanism and to lock a spinal fixation element within the receiver member. The bone anchor driver can have an outer shaft configured to engage and drive the outer closure mechanism into the receiver member, an inner shaft configured to engage and drive the inner closure mechanism into the receiver member, and an actuator movable between a first position in which the actuator applies a driving force to the outer shaft and a second position in which the actuator applies a driving force to the inner shaft, the actuator being configured to automatically move from the first position to the second position in response to a torque applied thereto.

The bone anchor and driver assembly can vary in a number of ways. For example, the actuator can move from the first position to the second position when a torque applied to the actuator exceeds a threshold torque of a torque limiting mechanism coupled between the actuator and the inner and outer shafts. In one embodiment, the threshold torque can cause the actuator to move from the first position to the second position when the outer closure mechanism is fully engaged with the receiver member to lock the polyaxial position of the receiver member with respect to the bone engaging member.

In another aspect, a method for operating a bone anchor driver is provided that in some embodiments includes actuating a driver to rotate a first shaft to drive a first closure mechanism onto a bone anchor. When a torque applied to the driver exceeds a threshold torque, the driver automatically moves from a first position decoupled from the first shaft and into a second position coupled with a second shaft to drive a second closure mechanism into the bone anchor.

The method for operating the bone anchor driver can vary in a number of ways. For example, driving the first closure mechanism into the bone anchor can lock a receiver member of the bone anchor in a fixed angular orientation with respect to a bone engaging member of the bone anchor, and driving the second closure mechanism into the bone anchor can lock a spinal fixation element in a fixed position within the receiver member of the bone anchor. In one embodiment, a torque limiter can cause the driver to move from the first position to the second position when a torque applied to the driver exceeds the threshold torque. The torque limiter can translate axially along a longitudinal axis of the first and second shafts when the driver moves between the first position and the second position. In other aspects, actuating the driver can include activating an external power source to cause the driver to rotate.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 3A is an exploded perspective view of an exemplary embodiment of a gear box of the bone anchor drivers of FIGS. 1, 2A, and 2B;

FIG. 3B is an exploded transparent, perspective view of the gear box of FIG. 3A;

FIG. 4C is another cross-sectional view of a longitudinal cross-section of the gear box of FIG. 3A;

FIG. 4D is another cross-sectional view of a longitudinal cross-section of the assembly FIG. 3A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided to apply a closure mechanism to a bone anchor. In one embodiment, a bone anchor drive is provided and includes an outer shaft configured to engage and drive an outer closure mechanism onto a receiver member of a bone anchor to lock a position of the receiver member with respect to a bone engaging member. The bone anchor driver can also include an inner shaft configured to engage and drive an inner closure mechanism into the receiver member to lock a spinal fixation element within the receiver member. The driver can be configured to automatically switch between driving the outer shaft and driving the inner shaft. For example, the driver can include a torque limiting mechanism that automatically switches between driving the outer shaft and the inner shaft. In this way, a single instrument can be used to both lock the angular orientation of the receiver member and lock (or "reduce") the spinal fixation element. The automatic switching can allow a two-piece closure assembly to be applied in a single step. The torque limiting mechanism can have a threshold force that causes the automatic switching and prevents an excess force from being applied to the closure assembly.

Accordingly, the methods and devices described herein allow performing a spinal surgical procedure in a simplified and time-saving manner. Because the bone anchor driver can be used to selectively drive both the outer and inner shafts to apply first and second closure mechanisms, a need for multiple instruments is reduced or eliminated, and surgeon's fatigue typically associated with repetitive motions can be decreased.

Figure 1:
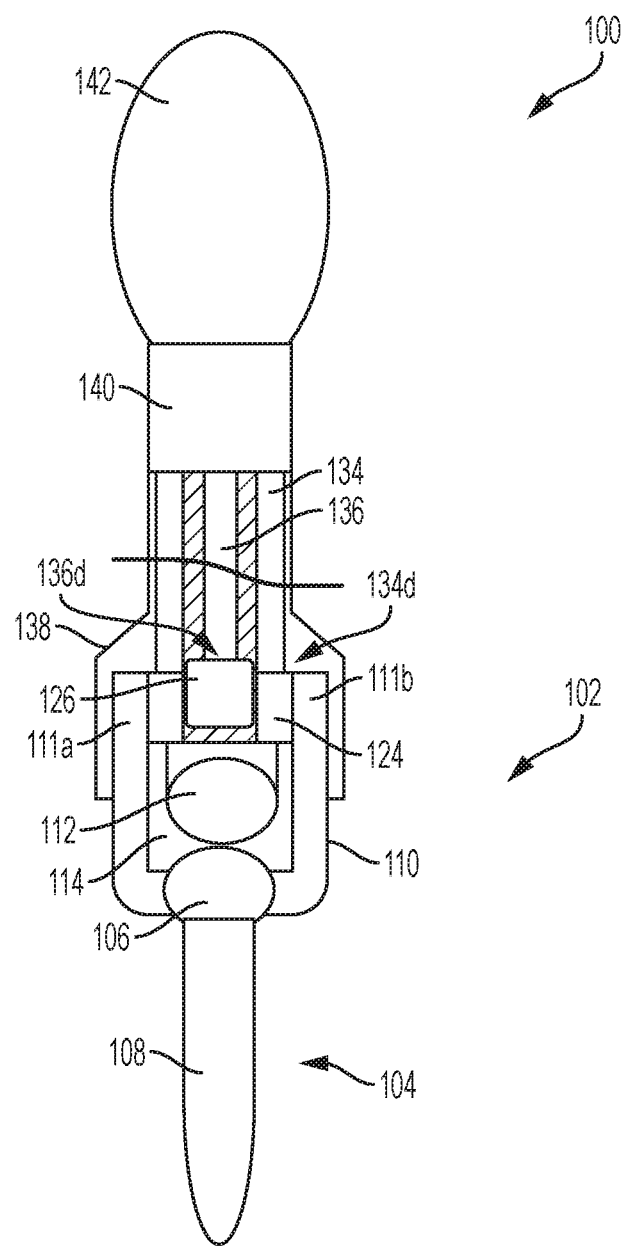
FIG. 1 is a schematic view of one exemplary embodiment of a bone anchor driver and a bone screw.

FIG. 1 illustrates one embodiment of a bone anchor driver 100 used to apply a closure mechanism to a bone anchor assembly 102. In the illustrated embodiment, the bone anchor assembly 102 is in a form of a polyaxial bone screw having a bone engaging member 104 with a proximal head 106 and a distal bone shank 108. The bone anchor assembly 102 also includes a receiver member 110 that polyaxially seats the head 106 of the bone engaging member 104, and that is configured to receive a spinal fixation element 112, such as a spinal rod, to couple the spinal fixation element 112 to the bone anchor assembly 102. The receiver member 110 shown in FIG. 1 has a proximal end having a pair of spaced apart arms 111A, 111B that define a recess or a slot therebetween for receiving the spinal fixation element 112 (e.g., a spinal rod).

The illustrated bone anchor assembly 102 also includes a compression member or cap 114 that is received within a central passage in the receiver member 110 and that has a distal surface that rests on the proximal head 106 of the bone engaging member 104, and a proximal surface that seats the spinal fixation element 112. The bone anchor assembly 102 further includes a closure assembly having an outer closure mechanism or set screw 124 and an inner closure mechanism or set screw 126. The outer set screw 124 is configured to be disposed within and to threadably mate with the arms 111A and 111B of the receiver member 110, and the inner set screw 126 is configured to be threadably disposed within the outer set screw 124.

The outer set screw 124 is operable to act on the compression member 114 to fix the bone anchor 104 relative to the receiver member 110. The inner set screw 126 is operable to act on the spinal fixation element or rod 112 to fix the spinal rod 112 relative to the receiver member 110. In this way, the closure assembly permits the bone anchor 104 to be fixed relative to the receiver member 110 independently of the spinal rod 112 being fixed to the receiver member 110.

A person skilled in the art will appreciate that the bone anchor driver and methods described herein can be used with various bone anchor assemblies, including various hooks and screws known in the art. The bone anchor assembly of FIG. 1 is described in more detail in U.S. Patent Application Publication No. 2014/0094849, entitled "Bone Anchor Assemblies," filed Sep. 17, 2013, the contents of which are incorporated herein by reference in their entirety. It should be appreciated that the embodiments described herein are not limited to any particular type of the bone anchor 104 and that the receiver member 110 can be coupled to the bone anchor 104 in any suitable manner. For example, the bone anchor 104 can be a polyaxial screw such that, prior to fixation, it can be adjustable to multiple angles relative to the receiver member 110. An exemplary polyaxial bone screw is described U.S. Pat. No. 8,313,516, which is hereby incorporated herein by reference in its entirety.

An exemplary bone anchor can also be a favored-angle polyaxial screw in which a cone of angulation is biased in one direction. The favored angle can aid in rod capture during a spinal procedure as the receiver member 110 can have additional range of motion in one direction, e.g., laterally away from the spinal column. Exemplary favored angle bone screws are described in U.S. Patent Application Publication No. 2014/0277159, which is hereby incorporated herein by reference in its entirety. Any other suitable types of bone anchors can be used additionally or alternatively.

Furthermore, in some embodiments, an exemplary bone anchor can be in a form of a monoaxial screw. In such embodiments, the compression member or cap 114 can be example, a typhoon cap, such as the Monarch Typhoon Cap available from DePuy Spine, Inc. of Raynham, Mass., and described in U.S. Pat. No. 6,755,829, which is incorporated herein by reference. An outer closure mechanism (e.g., outer set screw 124) can be used to cause the typhoon cap to capture a spinal fixation element (e.g., spinal fixation element 112) in a manner that allows movement of the bone anchor with respect to the spinal fixation element. An inner closure mechanism (e.g., inner set screw 126) can then be used to lock the position of the bone anchor with respect to the spinal fixation element.

As further shown in FIG. 1, the bone anchor driver 100 can be configured to apply the inner and outer set screws to the bone anchor 104. The bone anchor driver 100 can have a variety of configurations. In the embodiment illustrated in FIG. 1, the bone anchor driver 100 includes an outer shaft 134, an inner shaft 136 disposed within the outer shaft 134, a gear box 140 configured to deliver rotational force to selectively drive the outer and inner shafts 134, 136, and an activation handle 142 configured to be held and moved (e.g., rotated) by a surgeon. As shown in FIG. 1, the bone anchor driver 100 can optionally include an outer sleeve 138 positioned around the outer and inner shafts 134, 136 and having a proximal cylindrical portion and a distal flange having a distal increased diameter portion that receives therein the receiver member 110. The outer sleeve 138 can have any suitable configuration and, in some embodiments, can be operable as a counter-torque component.

The inner and outer shafts can have a variety of configurations to allow for mating with the closure assembly. In the illustrated embodiment, the distal end 134*d* of the outer shaft 134 can engage the outer set screw 124 seated in the receiver member 110 so that the outer shaft 134 can drive the outer set screw 124. Similarly, a distal end 136*d* of the inner shaft 136 can engage the inner set screw 126 seated within the outer set screw 124 in the receiver member 110 to drive the inner set screw 126. The inner and outer shafts 136, 134 can be configured to engage the inner and outer set screws 126, 124 in any suitable manner. For example, each shaft can include a distal drive tip, such as a hex tip, hex sock, or any other features for engaging a set screw as known in the art. The outer and inner shafts 134, 136 can drive the outer and inner set screws 124, 126, respectively, by applying a rotational force thereto. In this way, the outer and inner screws 124, 126 can be independently tightened to lock the orientation of the receiver member 110 with respect to the bone anchor 104 and to reduce the spinal fixation element 112.

The gear box 140 can have a variety of configurations, various exemplary embodiments of which will be disclosed in more detail below. As also discussed in more detail below, the gear box 140 can include a torque limiting mechanism configured to selectively drive one of the outer and inner shafts 134, 136 while the other remains stationary, and to automatically shift when a threshold torque is met to drive the other one of the outer and inner shafts. Although not shown herein, a person skilled in the art will appreciate that the bone anchor driver 100 can include various features that facilitate rotation of the outer and inner shafts 134, 136 with respect to each other.

The handle 142 can also have a variety of configurations. For example, the handle 142 can be a "T-handle," an "L-handle," or a handle having any other suitable configuration such that it is ergonomic and has a grip portion allowing it to be conveniently held by a surgeon. In the illustrated embodiment, the handle 142 extending proximally from the gear box 140 is rotatable by a surgeon to apply a rotational force to the outer and inner shafts 134, 136 via the gear box 140.

Figure 2B:
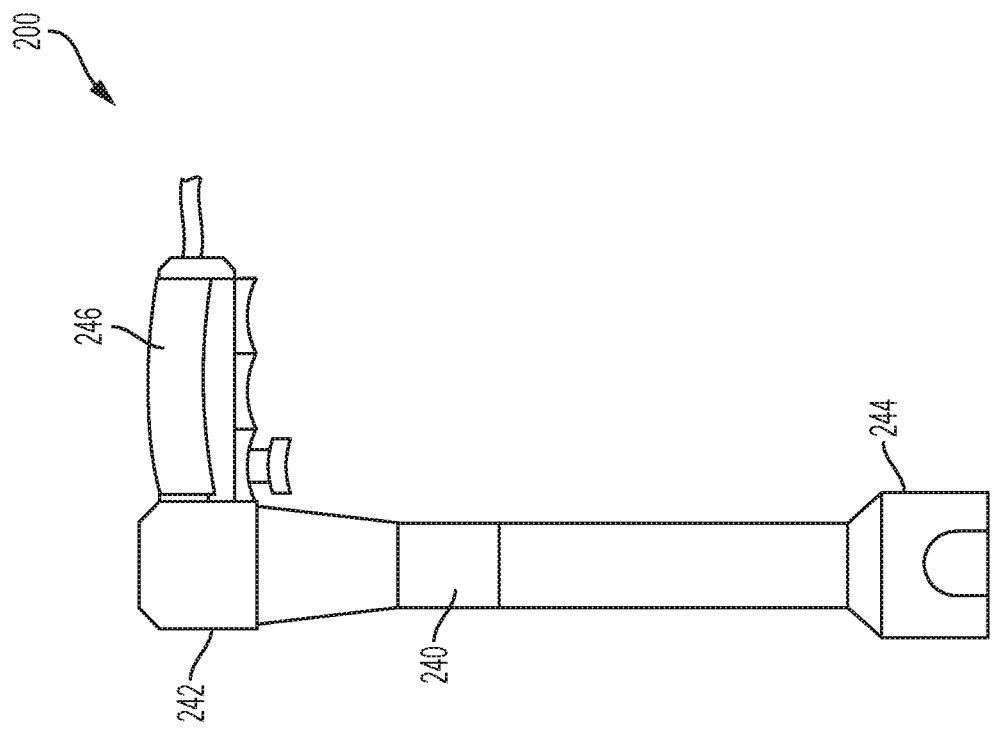
FIG. 2B is a schematic view of the bone anchor driver of FIG. 2A equipped with a counter-torque sleeve.
Figure 2A:
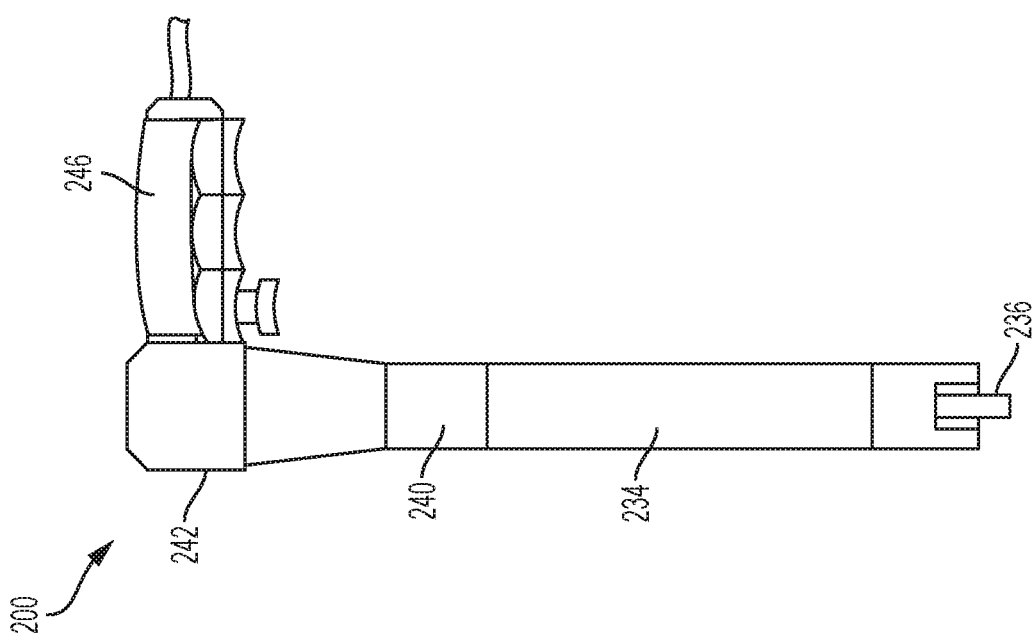
FIG. 2A is a schematic view of another exemplary embodiment of a bone anchor driver.

FIGS. 2A and 2B illustrate another embodiment of a bone anchor driver 200 that includes gear box 240 and a handle 242. In this embodiment, the handle 242 is configured to be operated using an external power source, unlike the manual handle of FIG. 1. As schematically shown in FIG. 2A, the handle 242 can be coupled to a powered driver 246 which can be connected to a main power supply via a wire and/or it can be battery-powered. The bone anchor driver 200 can be activated in any suitable manner. For example, the surgeon can activate a button, lever, or any other trigger mechanism for operating the screw driver 200 to apply a tightening torque to the outer set screw or inner set screw.

The gear box 240 of bone anchor driver 200 can be similar to gear box 140 of bone anchor driver 100. A gear box in accordance with the described embodiments, which can be implemented in a manually and/or power-driven bone anchor driver, will be discussed in more detail below. As further shown in FIG. 2A, the bone anchor driver 200 includes an outer shaft 234 and an inner shaft 236 disposed within a lumen of the outer shaft 234, only a distal portion of which is shown in FIG. 2A.

As shown in FIG. 2B, the bone anchor driver 200 can optionally include a counter-torque sleeve 244. The counter-torque sleeve 244 can be disposed around the outer shaft 234 (not shown in FIG. 2B) such that a proximal end of the counter-torque sleeve 244 is coupled to the handle 242. The counter-torque sleeve 244 can help maintain the receiver member of the bone anchor in a fixed position while the driver rotates the inner and outer set screws into the receiver member. While not shown, a person skilled in the art will appreciate that an inner portion of the counter-torque sleeve can be configured to engage non-rotatably an outer surface of the receiver member. The counter-torque sleeve 244 can be a component of the bone anchor driver 200 formed integrally with one or more components thereof. Alternatively, the counter-torque sleeve 244 can be a separate sleeve. It should be appreciated that any suitable type of a counter-torque sleeve can be utilized as embodiments are not limited in this respect.

As indicated above, the bone anchor drivers of FIGS. 1, 2A, and 2B each include a gear box for transferring a rotational force from the handle to the inner and outer shafts. FIGS. 3A and 3B illustrate one exemplary embodiment of a gear box. As shown, the gear box 300 (e.g., gear box 140 of the bone anchor driver 100 or gear box 240 of the bone anchor driver 200) includes a drive transfer member or actuator 302, an outer drive shaft or outer shaft 304, an inner drive shaft or inner shaft 306, and a torque limiting mechanism 308 disposed between the outer shaft 304 and the inner shaft 306. The drive transfer member 302, outer and inner shafts 304, 306, and torque limiting mechanism 308 can have a common central longitudinal axis B extending between proximal and distal ends 300*a*, 300*b* of the gear box 300, as shown in FIG. 3B.

Although not shown in FIGS. 3A and 3B, a distal end 304*b* of the outer shaft 304 can be coupled to or can be integrally formed with a proximal end 304*a* of the outer shaft 134, 234 of the bone anchor drivers of FIGS. 1 and 2A-2B. Similarly, a distal end 306*b* of the inner shaft 306 can be coupled to or can be integrally formed with a proximal end the inner shaft 136, 236 of the bone anchor drivers of FIGS. 1 and 2A-2B.

The drive transfer member 302, which is configured to transfer a rotational force from the handle to the torque limiting mechanism 308 to selectively drive the outer and inner shafts 304, 306, can have a variety of configurations. As shown, for example, in FIG. 4A, the drive transfer member 302 is generally configured as an elongate shaft and is disposed within a proximal end 300*a* of the gear box 300, and in particular extends through the outer shaft 304 and extends into the torque limiting mechanism 308 such that a distal end 302*b* of the drive transfer member 302 non-rotatably engages a proximal end 308*a* of the torque limiting mechanism 308. As a result, rotation of the drive transfer member will cause corresponding rotation of the torque limiting mechanism.

The distal end 302*b* of the drive transfer member 302 that engages the torque limiting mechanism 308 can have a cross-sectional shape that fits a complementary bore 309 formed in the proximal end 308*a* of the torque limiting mechanism 308. By way of a non-limiting example, the distal end 302*b* of the drive transfer member 302 can have a rectangular cross-sectional shape. However, it should be appreciated that the drive transfer member 302 can have a hexagonal, square, or any other cross-sectional shape that complements a shape of the bore 309 in the torque limiting mechanism 308, as embodiments are not limited to any particular configuration of the drive transfer member 302.

The proximal portion of the drive transfer member 302 that is positioned within a lumen 310 extending longitudinally through the outer shaft 304 can include any suitable features that facilitate rotation of the drive transfer member 302 with respect to the outer shaft 304. For example, in the illustrated embodiment, a bearing 312 can be interposed between the drive transfer member 302 and the outer shaft 304 to facilitate sliding and rotation of the drive transfer member 302 with respect to the outer shaft 304.

As shown in FIGS. 3A and 3B, the bearing 312 can be generally ring-shaped and can be disposed within a suitable bearing retainer, such as a bearing cage 314. The bearing cage 314 can be seated on an annular support ring 316 formed around the outer surface of the drive transfer member 302 approximately mid-way between the proximal and distal ends 302a, 302b thereof. In one embodiment, the bearing cage 314 can include cylindrical inner and outer washers 315, 317, as shown in FIGS. 3A and 3B, that seat the bearing cage 314 therebetween. One skilled in the art will appreciate that a bearing of any suitable configuration can be interposed in any manner between the drive transfer member 302 and the outer shaft 304. Further, it should be appreciated that any other features that facilitate interaction between the drive transfer member 302 and the outer shaft 304 can be used additionally or alternatively.

The outer shaft 304 of the gear box 300 can also have a variety of configurations. In the illustrated exemplary embodiment, the outer shaft 304 is a tubular elongate member having a lumen 310 formed therein that extends between the proximal and distal ends 304a, 304b thereof. An inner diameter of the lumen in the outer shaft 304 can be such that the inner shaft 306 and the torque limiting mechanism 308 fit within the inner lumen 310 of the outer shaft 304. As shown in FIG. 3B, for example, the lumen 310 includes four regions of different diameters. In particular, the lumen 310 includes a proximal portion 310a that is sized to slidably and rotatably receive the bearing assembly and a proximal portion of the drive transfer member 302; a proximal-mid portion 310b that is sized to slidably receive a proximal portion of the torque limiting mechanism 308 and a distal portion of the drive transfer member 302; a distal-mid portion 310c sized to slidably and rotatably receive a distal portion of the torque limiting mechanism 308 and a portion of the inner shaft 306; and a distal portion 310d that is sized to slidably and rotatably receive a distal portion of the inner shaft 306 and bearings 322, 324. The proximal-mid, distal-mid, and distal portions 310b, 310c, 310d can have successively increasing diameters that increase distally, and the proximal portion 310a can have a diameter that is greater than a diameter of the proximal-mid portion 310b and less than a diameter of the distal-mid portion 310c.

The inner surfaces of the proximal, proximal-mid, distal-mid, and distal portions 310a, 310b, 310c, 310d can have any suitable features that facilitate interaction between the outer shaft 304, the torque limiting mechanism 308, and the inner shaft 306. For example, as shown in FIG. 3B, a proximal end of the distal-mid portion 310c can have a ramp 311 having a contour that is complementary in shape to a contour of a ramp formed on the torque limiting mechanism 308 to facilitate movement of the torque limiting mechanism 308 within the outer shaft 304, as will be discussed in more detail below. A person skilled in the art will appreciate that the outer shaft 304 can have any suitable configuration, as embodiments are not limited in this respect.

Figure 4B:
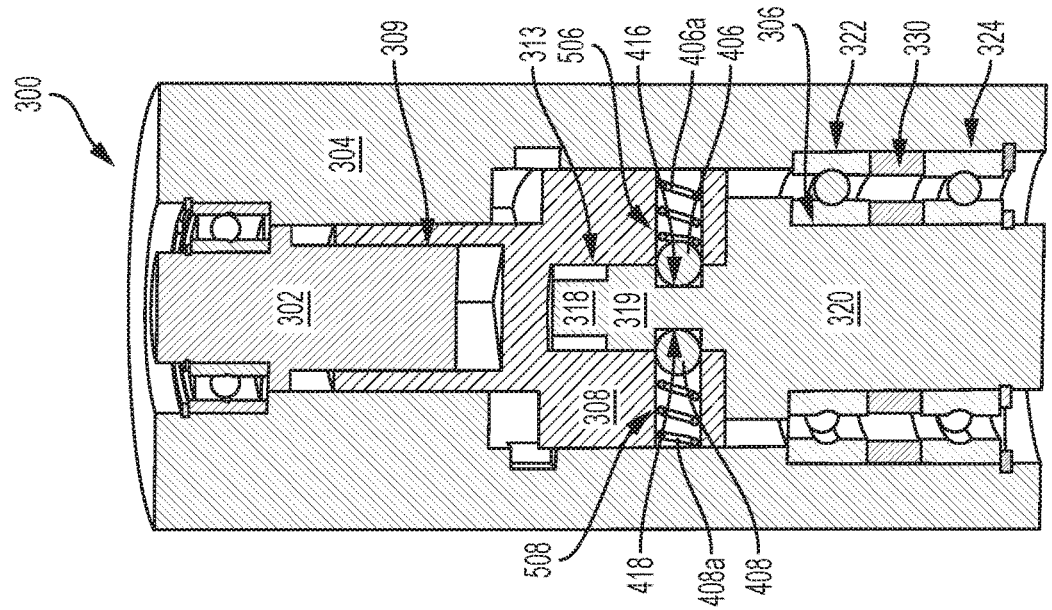
FIG. 4B is another cross-sectional view of a longitudinal cross-section of the gear box of FIG. 3A.
Figure 4A:
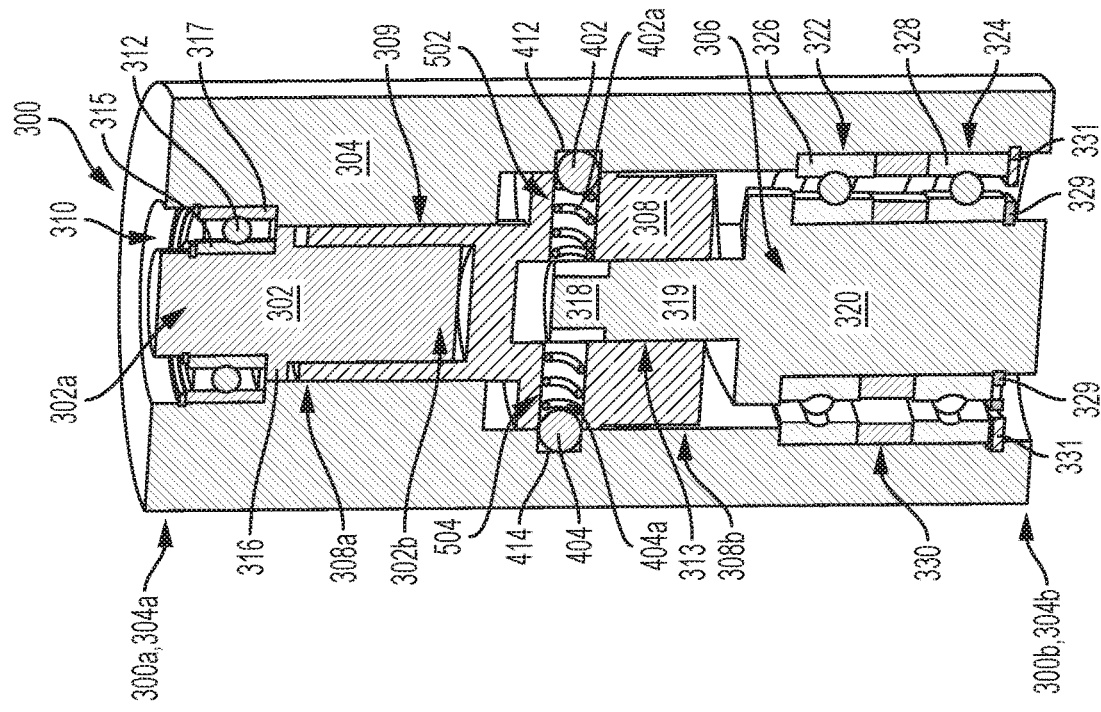
FIG. 4A is a cross-sectional view of a longitudinal cross-section of the gear box of FIG. 3A.

As shown in FIG. 4A, the inner lumen 310 (e.g., the distal-mid portion 310c thereof) of the outer shaft 304 can also include first complementary engaging members 412, 414 for engaging with respective first engaging members 402, 404 of the torque limiting mechanism 308 that are discussed in more detail below. In the illustrated exemplary embodiment, the first complementary engaging members 412, 414 can be in the form of recesses or detents formed in the inner sidewall of the outer shaft 304. The first complementary engaging members 412, 414 can be formed on opposite sides of the distal-mid portion 310c of the inner lumen 310 and they can be axially aligned. As shown in FIG. 4A, the first complementary engaging members 412, 414 are disposed at a first longitudinal position along a length of the outer shaft 304. The first complementary engaging members 412, 414 can have a configuration and size appropriate to engage with the first engaging members 402, 404 of the torque limiting mechanism 308 (e.g., balls or other engaging members), as also discussed in more detail below.

The inner shaft 306 can also have various configurations. As shown in FIGS. 3A and 3B, the inner shaft 306 can have proximal, middle, and distal portions 318, 319, 320 that can be separate components or that can be integrally formed with each other. The proximal, middle, and distal portions 318, 319, 320 have a common longitudinal axis B. As shown in FIGS. 3A and 3B, and additionally shown in FIG. 6, which schematically illustrates an overall shape of the inner shaft 306 (some details are omitted), the proximal portion 318 can have a smallest outer diameter among the proximal, middle, and distal portions 318, 319, 320, and the middle portion 319 can have an outer diameter that is greater than the outer diameter of the proximal portion 318 and less than an outer diameter of the distal portion 320.

The proximal and middle portions 318, 319 of the inner shaft 306 can be at least partially inserted into the torque limiting mechanism 308, as shown in FIGS. 4A-4D. As shown in FIGS. 3A and 3B, a bearing cap 323 can be inserted over the proximal portion 318 to facilitate interaction between the inner shaft 306 and the torque limiting mechanism 308. Any other suitable component can additionally or alternatively be used for this purpose.

Figure 6:
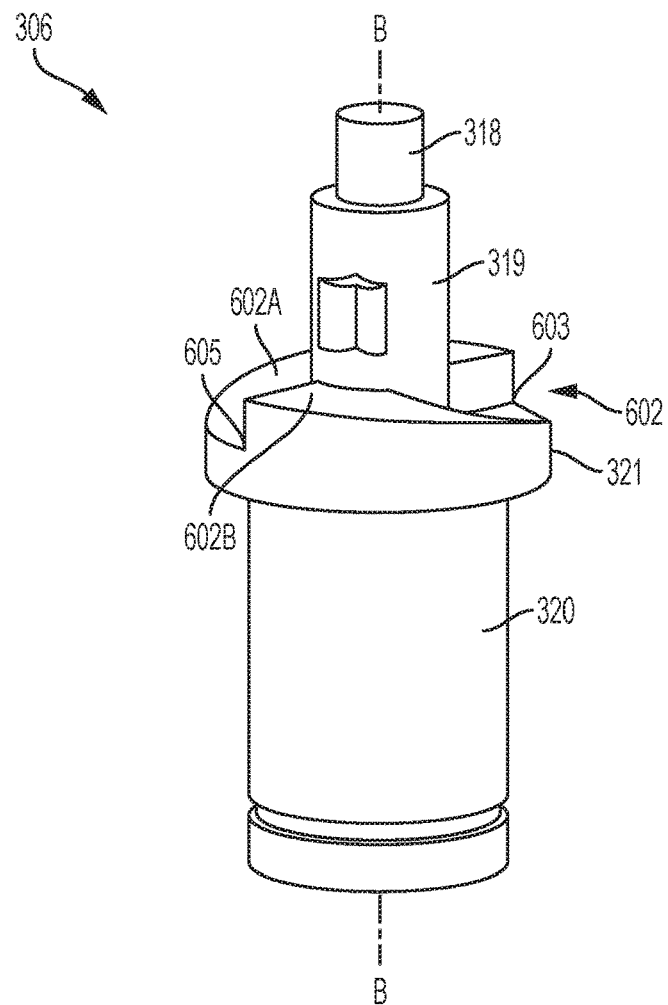
FIG. 6 is a schematic view of an exemplary embodiment of an inner shaft of the gear box of FIG. 3A.

One or more portions of the inner shaft 306 can be shaped and sized so as to engage with the torque limiting mechanism 308 which is configured to drive the inner shaft. For example, as shown in FIGS. 3A, 3B, and FIG. 6, the inner shaft 306 can have an outer collar 321 formed between the middle and distal portions 319, 320 thereof. As shown in FIG. 6, the outer collar 321 can include a ramp 602 formed thereon and having a contour that is configured to cause the torque limiting mechanism 308 to translate axially between a first position in which it is engaged with the outer shaft 304 and disengaged from the inner shaft 306, and a second position in which it is engaged with the inner shaft 306 and disengaged from the outer shaft 304.

In the illustrated embodiment, the ramp 602 includes a first portion 602A and a second portion 602B axially formed around the inner shaft 306 and interconnecting at first and second junctions 603, 605 located at opposite sides of a longitudinal axis B of the inner shaft 306. In one embodiment, the first and second portions 602A, 602B can have equal or substantially equal circumferences and they can be shaped and sized so that they mirror each other. For example, as shown in FIG. 6, the first portion 602A can have an upper surface that gradually declines (decreases) in height in a counterclockwise direction from the first junction 603 to the second junction 605. In a similar manner, the second portion 602B can have an upper surface that gradually declines (decreases) in height in a counterclockwise direction from the second junction 605 to the first junction 603. As a result, the ramp 602 will have first and second stepped portions formed at the first and second junctions 603, 605. A person skilled in the art will appreciate that the incline angle of each portion 602A, 602B can vary, but preferably that the incline angle is configured to cause the inner shaft 306 to move a sufficient distance axially so that the torque limiting mechanism 308 will move between the first and second portions 602A, 602B, as will be discussed in more detail below.

In some embodiments, the first and second stepped portions can have the same or substantially the same heights. It should be appreciated that the surfaces of the first and second portions 602Aa, 602B can have any suitable contours. For example, in some embodiments, the gradually inclined surfaces of the first and second portions 602A, 602B can be transverse to the longitudinal axis B of the inner shaft 306 throughout (i.e., the surfaces are flat), or they can be at least partially or entirely inwardly inclined. Furthermore, in some embodiments, one or more portions of the first and second portions 602A, 602B can be at least partially flat around a radial portion thereof such that the first and second portions 602A, 602B are not inclined through their entire surfaces.

Figure 5A:
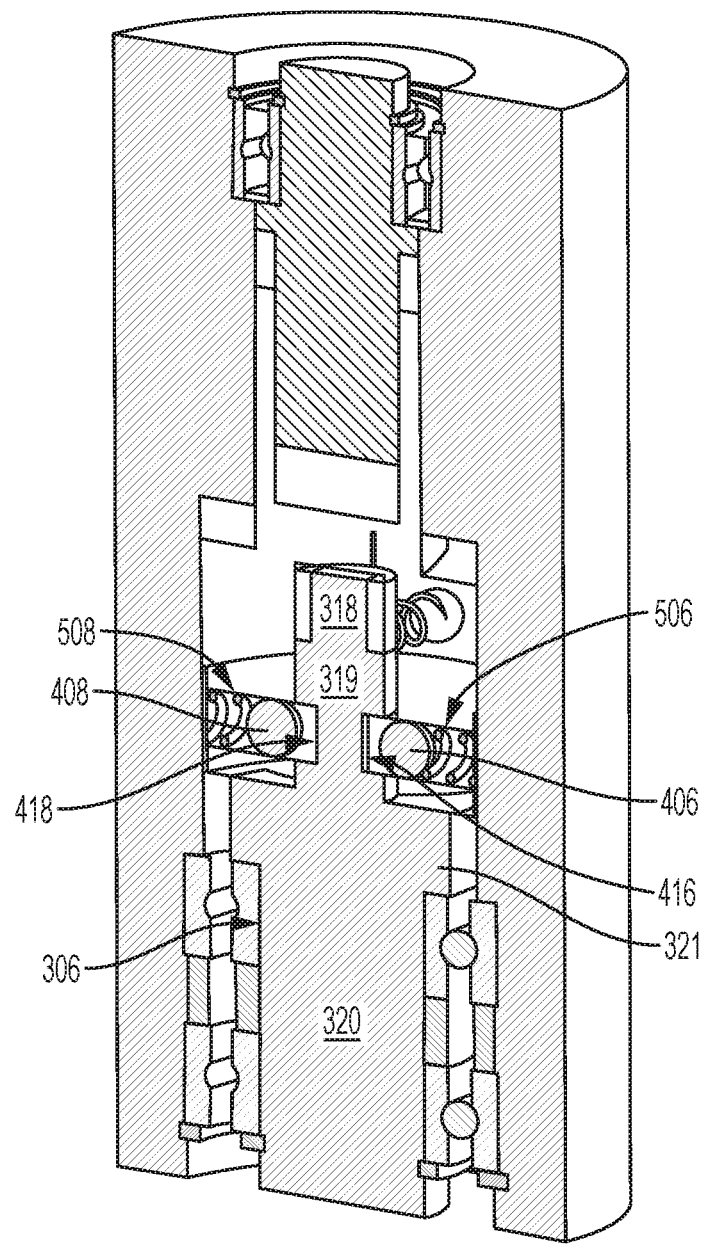
FIG. 5A is a transparent, longitudinal cross-sectional perspective view of the gear box of FIG. 3A.

As shown in FIGS. 4B and 5A, the middle portion 319 of the inner shaft 306 can include second complementary engaging members 416, 418 formed in opposite sides of the inner shaft 306 for engaging with respective second engaging members 406, 408 of the torque limiting mechanism 308 that are discussed in more detail below. In the illustrated exemplary embodiment, the second complementary engaging members 416, 418 can be recesses or detents formed in the outer surface of the inner shaft 306. The second complementary engaging members 416, 418 can have a configuration and size appropriate to receive the second engaging members 406, 408 of the torque limiting mechanism 308 (e.g., balls or other engaging members), as also discussed in more detail below.

In some embodiments, the distal portion 320 of the inner shaft 306 can be associated with axially spaced apart bearings 322, 324 interposed between the distal portion 320 of the inner shaft 306 and the outer shaft 304 to facilitate rotation of the inner shaft 306 and the outer shaft 304 with respect to each other. In the illustrated exemplary embodiment, as shown in FIGS. 3A-4B, the bearings 322, 324 can be disposed in respective cages 326, 328, and inner and outer washers or retaining members 329, 331, which can be semicircular or circular, hold the bearings 322, 324 in place. As also shown, the bearings 322, 324 can be spaced a distance apart along the outer surface of the inner shaft 306 so that an intermediate member 330 (e.g., circular or having other shape) is positioned therebetween around the inner shaft 306. The intermediate member 330 can include an inner portion 330a and an outer portion 330b that is configured to fit over the inner portion 330a such that the outer diameter of the intermediate member 330 matches the outer diameter of the bearing cages 326, 328.

It should be appreciated that any suitable number of bearings (e.g., one, two, three, or more), which can have any configuration (e.g., ring, ball, etc.) can be interposed between the inner and outer shafts 306, 304, as the described embodiments are not limited to any particular features that reduce rotational friction between the inner and outer shafts 306, 304.

Figure 5B:
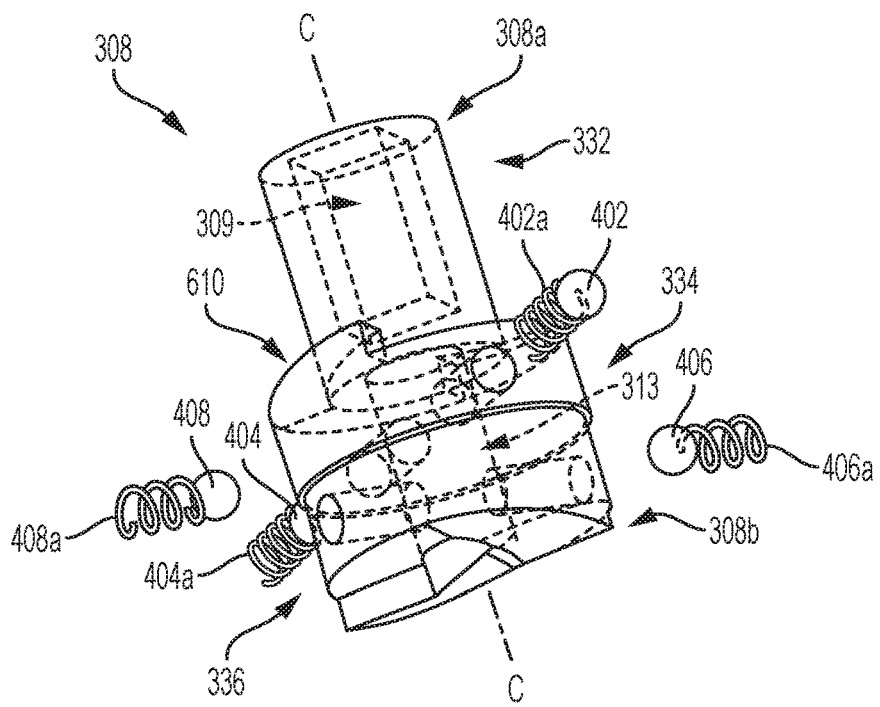
FIG. 5B is a transparent, perspective view of a torque limiting mechanism of the gear box of FIG. 5A.
Figure 5C:
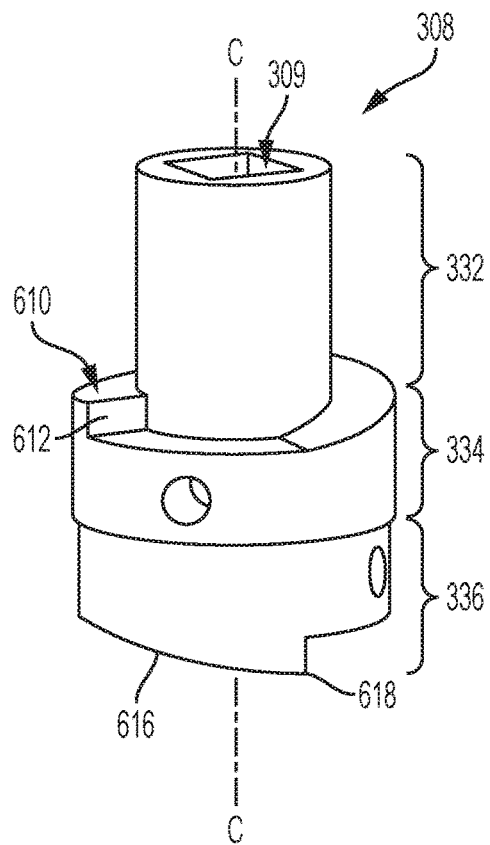
FIG. 5C is a schematic view of the torque limiting mechanism of FIG. 5B.

The torque limiting mechanism 308 can have a number of various configurations. As shown in FIGS. 4A and 4B, the torque limiting mechanism 308 extends between the inner and outer shafts 306, 304. The torque limiting mechanism 308 generally includes proximal, middle, and distal portions 332, 334, 336, as shown in FIGS. 5B-5C. The proximal portion 332 can have an outer diameter that is less than outer diameters of the middle and distal portions 334, 336, and the outer diameters of the middle and distal portions 334, 336 can be the same or approximately the same. One skilled in the art will appreciate that the proximal, middle, and distal portions 332, 334, 336 of the torque limiting mechanism 308 can have any suitable sizes and configurations.

The torque limiting mechanism 308 can receive a rotational force applied thereto by the drive transfer member 302. As discussed above, the torque limiting mechanism 308 can have a bore 309 extending distally from its proximal end 308a along a longitudinal axis C (shown in FIGS. 5B and 5C) of the torque limiting mechanism 308. The bore 309 can have a shape such that it is keyed to slidably and matably receive therein the drive transfer member 302. By way of a non-limiting example, the bore 309 can have a square or hexagonal shape to match a shape of the drive transfer member 302. The bore 309 can terminate proximally of the middle portion 334.

The rotational force applied to the torque limiting mechanism 308 by the drive transfer member 302 can be transferred to the outer shaft 304 or the inner shaft 306. As shown in FIG. 5B, the middle and distal portions 334, 336 of the torque limiting mechanism 308 include a bore 313 extending proximally along the longitudinal axis C thereof from the distal end 308b to approximately the proximal end of the middle portion 334 such that the bore 313 is not in communication with the drive bore 309. The bore 313 can receive the proximal portion 318 and at least part of the middle portion 319 of the inner shaft 306.

The torque limiting mechanism 308 can be disposed within the outer shaft 304 such that it can translate axially along the longitudinal axis of the outer shaft 304 and the longitudinal axis of the inner shaft 306. In the illustrated embodiment, the longitudinal axes B of the inner and outer shafts 306, 304 and the longitudinal axis C of torque limiting mechanism 308 coincide with each other.

To facilitate the axial movement of the torque limiting mechanism 308, a proximal facing surface of the middle portion 334 can be configured as a ramp 610 circumferentially formed around the outer surface of the middle portion 334 as shown in FIGS. 5B and 5C. The ramp 610 can be configured to engage a complementary surface formed in the outer shaft 304 such as, for example, ramp 311 formed at the distal-mid portion 310c of the lumen 310 extending through the outer shaft 304. The ramp 610 can have any suitable configuration. As shown in FIGS. 5B and 5C, the ramp 610 can have portions each having a surface that extends circumferentially around the outer surface of the torque limiting mechanism 308 from a raised stepped portion, such as a portion 612 (also shown in FIGS. 3A and 3B), while gradually decreasing in height in a clockwise direction. In some embodiments, the gradually declining surface of the ramp 610 can have one or more portions that can be inwardly inclined. Furthermore, one or more portions of the ramp 610 can be flat such that the ramp 610 may not be gradually declined throughout the entire surface thereof. It should be appreciated that the torque limiting mechanism 308 can have any other features that help it to move within the outer shaft 304.

The torque limiting mechanism 308 can further include features that facilitate its movement with respect to the inner shaft 306. Thus, a distal facing surface of the distal portion 336, which is a bottom of the torque limiting mechanism 308, can be shaped as a ramp 616 configured to couple to the surface of a ramp formed on the inner shaft 306, e.g., ramp 602 in FIG. 6 formed on the outer collar 321. The ramp 616, shown in FIGS. 3B, 5B and 5C, can be complementary to the ramp 602. For example, the ramp 616 can have portions that are complementary to the first and second portions 602A, 602B of the ramp 602.

The configuration of the ramp 616 allows the torque limiting mechanism 308 to engage the inner shaft 306 such that, when a certain threshold torque is reached, the torque limiting mechanism 308 rotates independent of the inner shaft 306 and translates axially upward or downward. In the illustrated embodiment, the ramp 616 can have formed thereon stepped surfaces complementary to the stepped surfaces of the ramp 602 on the inner shaft 306. For example, as shown in FIG. 5C, the ramp 616 can have a stepped edge 618 configured to mate with the first or second stepped portions formed at the first and second junctions 603, 605 of the ramp 602 formed on the outer collar 321 of the inner shaft 306.

The torque limiting mechanism 308 can be disposed between the outer and inner shafts 304, 306 so that it can automatically switch between being engaged with and rotatable with the outer shaft 304 while being disengaged from the inner shaft 306, and being engaged with and rotatable with the inner shaft 306 while being disengaged from the outer shaft 304. To selectively drive the outer and inner shafts 304, 306 in this manner, the torque limiting mechanism 308 includes engaging members configured to engage with respective complementary engaging members of the outer and inner shafts 304, 306. As shown in FIGS. 3A-5B, the middle portion 334 of the torque limiting mechanism 308 can include two first engaging members 402, 404 configured to engage with the first complementary engaging members 412, 414 of the outer shaft 304, and the distal portion 336 of the torque limiting mechanism 308 can include two second engaging members 406, 408 configured to engage with second complementary engaging members 416, 418 of the inner shaft 306.

In the illustrated exemplary embodiment, the first engaging members 402, 404 are positioned in a first plane and the second engaging members 406, 408 are positioned in a second plane that is spaced a distance apart from the first plane. As shown in FIGS. 4A and 5B, the first engaging members 402, 404 can be disposed within first bores 502, 504, respectively, extending across the middle portion 334 transverse to the longitudinal bore 313 in the torque limiting mechanism 308. The second engaging members 406, 408 can be disposed within second bores 506, 508, respectively, extending across the distal portion 336 transverse to the longitudinal bore 313. As shown in FIG. 4A, the first bores 502, 504 can extend approximately through a mid-portion of the middle portion 334 along an axis that is substantially perpendicular to a longitudinal axis C of the torque limiting mechanism 308. In a similar manner, as shown in FIG. 4B, the second bores 506, 508 can extend approximately through a mid-portion of the distal portion 336 along an axis that is substantially perpendicular to the longitudinal axis C of the torque limiting mechanism 308. In some embodiments, however, the first bores 502, 504 and/or the second bores 506, 508 can extend through the torque limiting mechanism 308 at an angle with respect to the longitudinal axis C.

The first bores 502, 504 and the second bores 506, 508 can extend through the torque limiting mechanism 308 such that they each form openings on the outer surface thereof. The first engaging members 402, 404 and the second engaging members 406, 408 can engage with respective first complementary engaging members 412, 414 and the second complementary engaging members 416, 418 through the openings of the first and second bores 502, 504, 506, 508.

In the illustrated embodiments, the second bores 506, 508 can be spaced radially apart from the first bores 502, 504 such that an axis of the second bores 506, 508 extend transverse, e.g., perpendicular, to an axis of the first bores 502, 504. It should be appreciated that although the first bores 502, 504 are shown to extend along the same axis, in some embodiments, the first bore 502 can extend at an angle to the first bore 504. Similarly, the second bore 506 can extend at an angle to the second bore 508.

In some embodiments, as discussed above, the first complementary engaging members 412, 414 of the outer shaft 304, which are configured to engage with the first engaging members 402, 404, can be recesses, detents, or any other suitable features formed in the surface of the lumen 310 of the outer shaft 304. As shown, for example, in FIG. 4A, the first recesses 412, 414 can be formed in the same plane. As shown in FIG. 4B, the second complementary engaging members 416, 418 of the inner shaft 306, which are configured to engage with the second engaging members 406, 408, can also be recesses, detents, or any other suitable features formed in the outer surface of the middle portion 319 of the inner shaft 306. The second recesses 416, 418 can be formed in the same plane, which is distally spaced apart from the plane in which the first recesses 412, 414 are formed.

The first engaging members 402, 404 and the second engaging members 406, 408 can have any suitable configurations, including configurations that differ between the first engaging members 402, 404 and the second engaging members 406, 408. In the illustrated embodiment, each of the first and second engaging members 402, 404, 406, 408 is in the form of a ball or other retaining element. Each engaging member can be biased into engagement with a respective complementary engaging member. As shown in FIG. 4A, the first engaging member or ball 402 is biased into engagement with the first complementary engaging member or recess 412 in the outer shaft 304 by a first spring 402A, and the first engaging member or ball 404 is biased into engagement with the first complementary engaging member or recess 414 formed in the outer shaft 304 by a first spring 404A. Second springs 406A, 408A can bias the second engaging members or balls 406, 408, respectively, into engagement with the second complementary engaging members or recesses 416, 418 formed in the inner shaft 306.

When the torque limiting mechanism 308 is in the first position in which it is engaged with the outer shaft 304 and is disengaged from the inner shaft 306, the first balls 402, 404 can protrude from the first bores 502, 504 and into the first recesses 412, 414. The second balls 406, 408 will not be aligned with the second recesses 416, 418, and thus the second balls 406, 408 will be disposed within the second bores 506, 508. In a similar manner, when the torque limiting mechanism 308 is in the second position in which it is engaged with the inner shaft 306 and is disengaged from the outer shaft 304, the second balls 406, 408 can protrude from the second bores 506, 508 and into the second recesses 416, 418. The first balls 402, 404 will not be aligned with the first recesses 412, 414, and thus the first balls 402, 404 will be disposed within the first bores 502, 504. FIG. 4D illustrates the torque limiting mechanism 308 turned 90 degrees along its longitudinal axis C from the second position shown in FIG. 4B such that the first engaging members 402, 404 for engaging with the first complementary engaging member (recesses, in this example) 412, 414 formed in the lumen 310 of the outer shaft 304 are visible.

It should be appreciated that the first engaging members 402, 404 and the second engaging members 406, 408 are shown as balls that are spring-biased by way of example only, as any other engaging members configured to engage complementary engaging members of the inner and outer shafts can be used additionally or alternatively. For example, any suitable biasing elements other than a spring can be used. As another variation, any suitable object can be used that can be biased by a biasing element. Furthermore, the first engaging members 402, 404 and the second engaging members 406, 408 can be other types of engaging members, as embodiments are not limited to any specific configuration of the first and second engaging members.

As shown, for example, in FIG. 3A, in one embodiment, the torque limiting mechanism 308 can include a closure member 340 that can be disposed axially around the distal portion 336 of the torque limiting mechanism 308 to enclose the openings of the second bores 506, 508 in the torque limiting mechanism 308.

The recesses 412, 414, 416, 418 can be shaped to retain the engaging members, e.g., balls, so as to prevent the balls from being rotated out of the recesses until a predetermined torque is applied thereto. The recesses can thus have a configuration that results in a desired threshold force. By way of non-limiting example, each recess can have a generally hemi-cylindrical shape, however one or more of the sidewalls can be angled so as to allow the ball to be rolled out of the recess in a circumferential direction. The angle of the sidewall can be adjusted as desired to achieve the necessary threshold torque. Exemplary embodiments of recess configurations will be discussed in more detail below. A person skilled in the art will appreciate that various techniques can be used to retain an engaging member in an engaged position until a desired threshold force is applied to cause the engaging member to become disengaged. Furthermore, in embodiments in which engaging members other than balls biased by respective springs are utilized additionally or alternatively, the recesses can be configured accordingly, to receive and retain those engaging members.

The described devices and methods allow automatically switching between driving the inner shaft and driving the outer shaft. With reference to FIGS. 4A-4D, the bone anchor driver having a torque limiting mechanism 308 can be used to selectively drive an outer shaft to tighten an outer closure mechanism or an inner shaft to tighten an inner closure mechanism. The torque limiting mechanism 308, driven (manually or electrically) via the drive transfer member 302, can automatically switch between driving the outer and inner shafts 304, 306, which can be done repeatedly. For example, a surgeon can actuate a handle, such as handle 142 (FIG. 1) or handle 242 (FIGS. 2A and 2B), to deliver a rotational force to the drive transfer member 302 that, in turn, applies that force to the torque limiting mechanism 308.

As shown in FIG. 4A, when the rotational force is applied to the torque limiting mechanism 308, the torque limiting mechanism 308 can be in a first position in which it is engaged with the outer shaft 304 and is disengaged from the inner shaft 306. In the first position, the first engaging members 402, 404 are engaged with and disposed in the same plane as the first complementary engaging members 412, 414. For example, in one embodiment, as shown in FIG. 4A, the first balls 402, 404 are biased by the springs 402A, 404A into engagement with the complementary recesses 412, 414 formed in the outer shaft 304. In this way, the rotational force applied to the torque limiting mechanism is transmitted to the outer shaft 304 to drive the outer shaft 304. As discussed above, the distal end 304b of the outer shaft 304 can be coupled to or can be integrally formed with outer shaft 134 such that the rotational force applied to the outer shaft 304 causes an outer closure mechanism (e.g., outer set screw 124 in FIG. 1) to rotate into the receiver member 110.

FIG. 4C illustrates the torque limiting mechanism 308 turned 90 degrees along its longitudinal axis C from the first position shown in FIG. 4A such that only the second engaging members 406, 408 for engaging with the second complementary engaging member 416, 418 (recesses, in this example) of the inner shaft 306 are visible. As shown in FIG. 4C, in the first position, the second balls 406, 408 are misaligned axially with respect to the second complementary recesses 416, 418 formed in the inner shaft 306 and the torque limiting mechanism 308 is thus not engaged with the inner shaft 306.

The torque limiting mechanism 308 as shown in FIG. 4A will continue to rotate the outer shaft 304 as long as the torque applied thereto is less than or equal to a first threshold torque. The first threshold torque can have any suitable value(s), as the described embodiments are not limited in this respect.

When the outer set screw 124 is fully engaged with the receiver member (e.g., receiver member 110 in FIG. 1) to lock the polyaxial position of the receiver member with respect to the bone engaging member (e.g., bone engaging member 104 in FIG. 1), the torque required to rotate the outer set screw 124 will increase and thus exceeds the first threshold torque. For example, in the illustrated embodiment, when resistance from the outer set screw 124 becomes such that the torque applied to the torque limiting mechanism 308 exceeds the first threshold torque, the bias of each of the springs 402A, 404A can be overcome to cause the balls 402, 404 to disengage from the recesses 412, 414 such that the torque limiting mechanism 308 becomes disengaged from the outer shaft 304. When it becomes disengaged from the outer shaft 304, the torque limiting mechanism 308 can rotate independent of the outer shaft 304.

A torque that exceeds the first threshold torque can cause the torque limiting mechanism 308, driven by the drive transfer member 302, to automatically switch from the first position to the second position in which it is disengaged from the outer shaft 304 and becomes engaged with the inner shaft 306. Because the switch from the first position to the second position (and vice versa) occurs automatically, without an action by an operator (e.g., surgeon), it can be perceived by the surgeon as a single operation, which improves overall experience of the surgeon and simplifies the surgery.

To transition from the first position to the second position, the torque limiting mechanism 308 can move distally to the position as shown in FIG. 4B. As the torque limiting mechanism 308 continues to rotate independent of the outer shaft, it moves distally due to the declining ramp 602. The second engaging members 406, 408 will move into alignment and engagement with the complementary second engaging members 416, 418 formed in the inner shaft 306. For example, in the illustrated exemplary embodiment, the balls 406, 408 can be biased by the springs 406A, 408A to engage with the recesses 416, 418 formed in the inner shaft 306, as shown in FIG. 4B. In the second position, the balls 402, 404 are disposed distal of the recesses 412, 414 formed in the outer shaft 304. In this way, the balls 402, 404 move with the torque limiting mechanism 308 while remaining disengaged from the outer shaft 304.

Once the torque limiting mechanism 308, while being disengaged from the outer shaft 304, engages with the inner shaft 306 in this manner, the force applied to the torque limiting mechanism 308 is transmitted to the inner shaft 306 to thus drive the inner shaft 306.

Driving the inner shaft 306 locks a spinal fixation element, such as the spinal fixation element or rod 112 shown in FIG. 1, in a fixed position within the receiver member 110 of the bone anchor assembly 102. The spinal fixation element 112 can be said to be "reduced." As discussed above, the distal end 306b of the inner shaft 306 can be coupled to or can be integrally formed with inner shaft 136 or 236. Thus, the rotational force applied to the inner shaft 306 by the torque limiting mechanism 308 in the second position can cause an inner closure mechanism (e.g., inner set screw 126 in FIG. 1) to tighten to thereby lock the spinal fixation element 112 in a fixed position within the receiver member 110.

In some embodiments, the inner shaft 306 engaged with the torque limiting mechanism 308 as shown in FIG. 4B can continue rotating until the inner set screw 126 is tightened and a torque applied to the torque limiting mechanism 308 exceeds a second threshold torque. For example, when resistance from the inner set screw 126 becomes such that the torque applied to the torque limiting mechanism 308 exceeds the second threshold torque, the bias of each of the springs 406A, 408A can be overcome to cause the balls 406, 408 to disengage from the recesses 416, 418 such that the torque limiting mechanism 308 becomes disengaged from the inner shaft 306. The second threshold torque can have any suitable value, which can be the same or different from a value of the first threshold torque.

When the torque applied to the torque limiting mechanism 308 exceeds the second threshold torque, the torque limiting mechanism 308 can switch from the second position to the first position in which it is engaged with the outer shaft 304 and is disengaged from the inner shaft 306. Thus, the bone anchor driver can be operated such that the torque limiting mechanism 308 can automatically and repeatedly switch between driving the outer and inner shafts 304, 306 when the respective first and second threshold torques are exceeded.

With reference to FIGS. 4A-4D, 5B, 5C and 6, the configuration of complementary ramps formed on the inner and outer shafts 306, 304 and the torque limiting mechanism 308 will cause the torque limiting mechanism 308 to translate axially between the first and second positions for driving the outer and inner shafts, respectively. For example, when the torque limiting mechanism 308 is in the first position for driving the outer shaft, as shown in FIGS. 4A and 4C, the more proximal ramp 610 on the torque limiting mechanism 308 will be in close mating engagement with the complementary ramp 311 formed at the distal-mid portion 310c of the lumen 310 extending through the outer shaft 304. The more distal ramp 616 on the torque limiting mechanism 308 will be spaced apart from ramp 602 formed in the inner shaft 306, as shown in FIG. 4A.

When the torque limiting mechanism moves from the first position to the second position for driving the inner shaft, the torque limiting mechanism 308 will rotate independent of and relative to the inner and outer shafts 306, 304. Such clockwise rotation of the torque limiting mechanism will cause ramp 610 to rotate relative to ramp 311. As ramp 610 is rotated in a clockwise direction relative to ramp 311, the increasing height of ramp 610 and of ramp 311 will cause the torque limiting mechanism 308 to move distally away from ramp 610 on the outer shaft 304 and to move toward ramp 602 on the inner shaft 306. In particular, the stepped portions of the ramp 610 (only portion 612 is shown in FIG. 5C) on the torque limiting mechanism will move out of engagement with the stepped portions on the ramp 311 on the outer shaft, and the ramps 610, 311 will ride against one another, increasing in height through their relative rotation to cause distal movement of the torque limiting mechanism. Once the torque limiting mechanism is moved to a distal-most position, the torque limiting mechanism will be in the second position for driving the inner shaft 306. The more distal ramp 616 on the torque limiting mechanism will be in mating engagement with the ramp 602 on the inner shaft. In particular, the declining portions of the ramps can slide into engagement with one another until the stepped portions of ramp 616 engage with the stepped portions formed at the first and second junctions 603, 605 of ramp 602. Thus, in the second position, the ramp 616 of the torque limiting mechanism 308 is in full engagement with and contacts the surface of the ramp 602 formed in the inner shaft 306, as shown in FIGS. 4B and 4D.

When switching from driving the inner shaft 306 in the second position to driving the outer shaft 304 in the first position, the geometry of the ramp 602 on the inner shaft will similarly cause the torque limiting mechanism to ride up the ramp 602 and move proximally toward the first position. As a result, ramp 616 of the torque limiting mechanism 308 will no longer sit in contact with the surface of the ramp 602.

As one skilled in the art will appreciate, a torque applied to the torque limiting mechanism can be measured in any suitable manner. For example, a suitable component (e.g., a handle) of the bone anchor driver can include one or more sensors configured to measure the torque. A torque applied to both inner and outer shafts can be measured. Any other parameters, such as, for example, a driving speed of the driver (e.g., in RPM (revolutions per minute)) can be measured as well. In some embodiments, the torque and/or the driving speed can be measured continuously when the bone anchor driver is in use. Data connected by the sensor(s) and/or any other measuring elements can be visually displayed on a suitable display such that a surgeon can monitor it during a surgery.

In some embodiments, the first and second threshold torques can be adjustable, which can be performed manually or automatically. Thus, a torque limiting mechanism of a bone anchor driver implemented using the described embodiments can be adjusted to switch between driving outer and inner shafts depending on different threshold torque levels.

In some embodiments, a torque can be adjusted by changing one or more characteristics of first and second engaging members and/or first and second complementary engaging members. For example, the torque can depend on angle(s) of bores 502, 504, 506, 508 holding engaging members 402, 404, 406, 408 with respect to a longitudinal axis of the torque limiting mechanism. As an example, a more acute angle of a bore can require less torque to switch between the first and second positions of the torque limiting mechanism.

Figure 7:
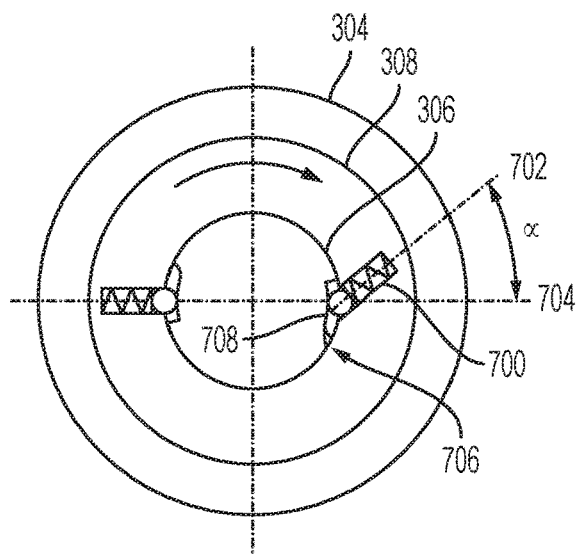
FIG. 7 is a schematic top, cross-sectional view illustrating a groove of an inner shaft of the gear box of FIG. 3A.

Furthermore, the features of first and second engaging members such as a force applied by a biasing element (e.g., a spring), configuration of the biasing element and the retaining element (e.g., a ball), and their position with respect to each other can affect the torque to be used to switch between driving the outer and inner shafts of the bone anchor driver. FIG. 7 illustrates an example of an angle α between a longitudinal axis 702 of a bore 700, e.g., second bore 506 or 508 for engagement with the inner shaft, (and therefore a longitudinal axis of a spring or other biasing member with coincides with the longitudinal axis of the bore) and an axis 704 that is transverse to the longitudinal axis of the torque limiting mechanism that can be adjusted to adjust the torque. As the angle α decreases, the greater torque value(s) can be required to switch between engaging the outer and inner shafts.

Additionally or alternatively, in some embodiments, the contour of complementary engaging members, such as recesses or detents formed in the inner and outer shafts, can be modified to adjust the first and second threshold torques. The recesses or detents can have a ramp formed on inner surfaces thereof, and an angle of the ramp can be modified to adjust the first and second threshold torques. The complementary engaging members can be shaped and sized so that to adjust an angle at which an engaging member, such as a ball or other retention element, engages with the respective complementary engaging. In addition to illustrating that an angle alignment of the engaging member can affect the torque limits, FIG. 7 illustrates schematically, by an arrow 706, that different configurations of a ramp 708 formed in the complementary engaging member can affect the torque limits.

Figure 8B:
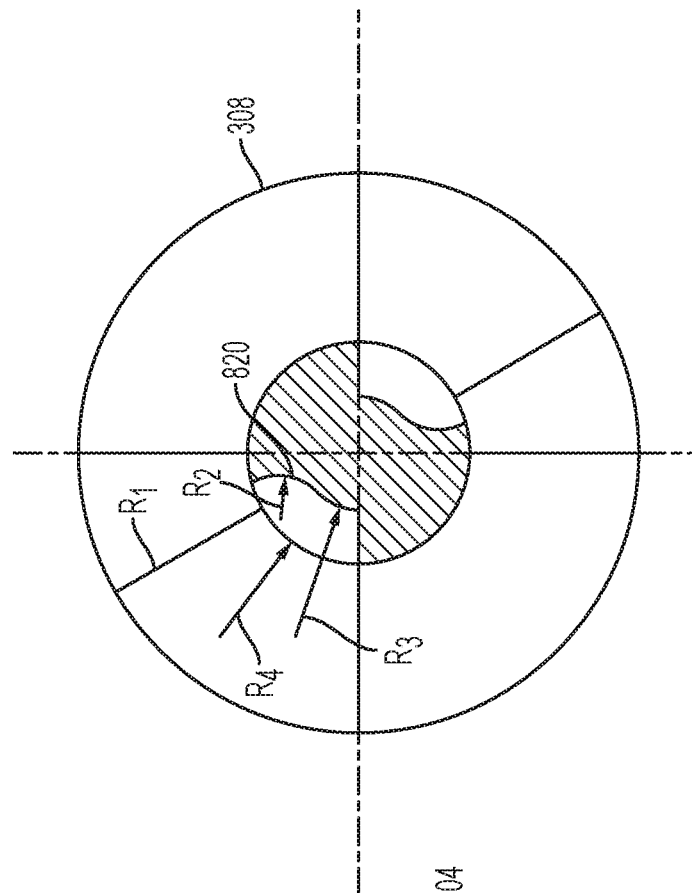
FIG. 8B is a schematic top, cross-sectional view illustrating a complementary engaging member of an inner shaft of the gear box of FIG. 3A.
Figure 8A:
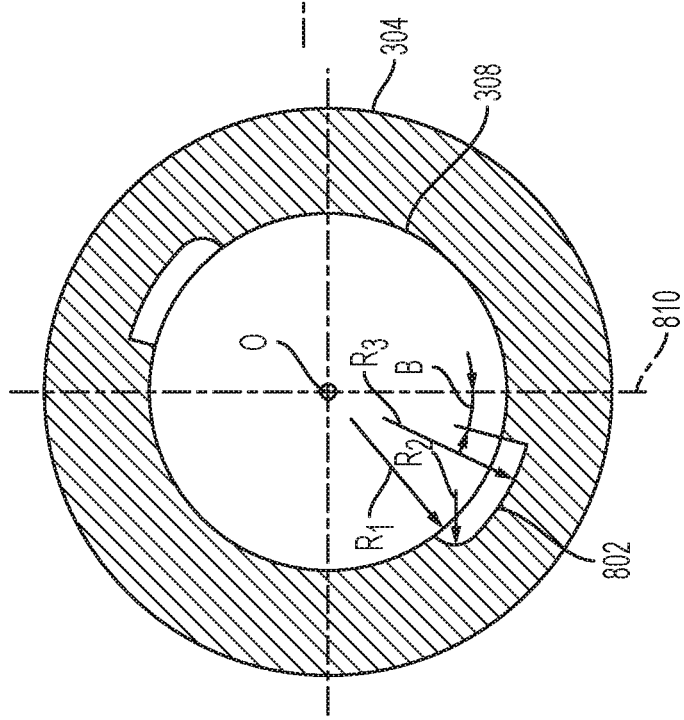
FIG. 8A is a schematic top, cross-sectional view illustrating a complementary engaging member of an outer shaft of the gear box of FIG. 3A.

FIG. 8A illustrates the geometry of a first complementary engaging member 802 (e.g., first complementary engaging member 412 or 414) of the outer shaft 304 for engaging with a first engaging member of the torque limiting mechanism 308 that can affect at least one of the first and second threshold torques. As shown, the geometry of the first complementary engaging member 802 can be characterized by various parameters such as, for example, a first radius R1 measured from a center O of outer shaft 304 (which coincides with the center of the torque limiting mechanism 308) to a plane extending through an outer surface of the engaging member 802 parallel to the longitudinal axis of the outer shaft 304, a second radius R2 of the inner surface of the engaging member 802, a third radius R3 measured from the center O of outer shaft 304 to an inner surface of the engaging member 802, and an angle θ between the third radius R3 and an axis 810 that is transverse to the common central longitudinal axis of the outer shaft 304 and the torque limiting mechanism 308. In one example, the first radius R1 is about 12.5 mm, the second radius R2 is about 2 mm, the third radius R3 is about 14.5 mm, and the angle θ is about 15°.

As another example, FIG. 8B illustrates the geometry of a second complementary engaging member 820 (e.g., second complementary engaging member 416 or 418) of the inner shaft 306 for engaging with a second engaging member of the torque limiting mechanism 308 that can affect at least one of the first and second threshold torques. As shown, the geometry of the second complementary engaging member 820 can be characterized by various parameters such as, for example, a first radius R1 measured from the outer surface of the torque limiting mechanism 308 to a plane extending through an outer surface of the engaging member 820 parallel to the longitudinal axis of the inner shaft 306, a second radius R2 of the inner surface of the engaging member 820, and a third radius R3 measured from the outer surface of the torque limiting mechanism 308 to an inner surface of the engaging member 820. In the illustrated embodiment, the threshold torque primarily depends on the radius R2. The radius R2 can have any suitable value defined by a shape of the inner surface of the second complementary engaging member 820 (e.g., linear, curved, or any other shape). When the shape of the inner surface of the engaging member 820 is such that the inner surface is aligned with the angle of entry of an engaging member (e.g., second engaging member 406 or 408), a threshold torque required to switch the torque limiting mechanism 308 from driving the outer shaft 304 to driving the inner shaft 306 can decrease. In other words, if the inner surface of the second complementary engaging member 820 is such that it is easier for the engaging member to escape the recessed surface of the complementary engaging member 820 as the outer shaft 304 is driven, a smaller threshold torque can be required for the torque limiting mechanism 308 to switch from driving the outer shaft 304 to driving the inner shaft 306.

It should be appreciated that the first and second complementary engaging members 802, 820 can have any suitable contours and various features of the contours can be adjusted to thereby adjust at least one of the first and second threshold torques used to switch the bone anchor driver from driving the inner and outer shaft.

Having thus described at least one illustrative embodiment, various alterations, modifications and improvements will readily occur to those skilled in the art.

For example, in one embodiment, a bone anchor driver can be provided that includes a torque limiting mechanism configured to automatically switch between a first position in which the torque limiting mechanism is disengaged from the outer shaft and is engaged with the inner shaft, and a second position in which the torque limiting mechanism is disengaged from the inner shaft and is engaged with the outer shaft.

Further, although in the illustrated embodiments, an outer closure mechanism is configured to mate to a receiver member for locking a polyaxial position of the receiver member with respect to the bone engaging member, and an inner closure mechanism is configured to lock a spinal fixation element within the receiver member, in one embodiment, the outer closure mechanism can be configured to lock a spinal fixation element within the receiver member, and the inner closure mechanism can be configured to lock a polyaxial position of the receiver member with respect to the bone engaging member.

As another variation, while in the illustrated embodiment a bone anchor assembly is in a form of a polyaxial bone screw, as mentioned above, the bone anchor assembly can be in a form of a monoaxial bone screw. In such an embodiment, a two-piece locking cap can be used. For example, an outer closure mechanism can coupled with a typhoon cap and it can be driven to capture a spinal fixation element (e.g., a spinal rod) while allowing for translation of the monoaxial bone screw along the spinal fixation element. An inner closure mechanism can then be driven to lock the bone anchor assembly with respect to the spinal fixation element.

The devices discussed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the embodiments described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the methods and devices based on the above-described embodiments. Accordingly, the methods and devices are not to be limited by what has been particularly shown and described, except as indicated by the appended claims. All publications and references cited herein are expressly incorporated herein by reference in their entirety.

What is claimed is:

1. A method for operating a bone anchor driver, comprising:
   actuating a driver to rotate a first shaft to drive a first closure mechanism onto a bone anchor, wherein, when a torque applied to the driver exceeds a threshold torque, the driver automatically moves from a first position coupled to the first shaft and into a second position decoupled from the first shaft and coupled with a second shaft to drive a second closure mechanism into the bone anchor, and wherein a proximal portion of the first shaft and a proximal portion of the second shaft are operatively coupled to a torque limiter and a distal end of the first shaft is adjacent to a distal end of the second shaft.

2. The method of claim 1, wherein driving the first closure mechanism onto the bone anchor locks a receiver member of the bone anchor in a fixed angular orientation with respect to a bone engaging member of the bone anchor, and driving the second closure mechanism into the bone anchor locks a spinal fixation element in a fixed position within the receiver member of the bone anchor.

3. The method of claim 2, wherein the applied torque exceeds the threshold torque when the first closure mechanism is fully engaged with the receiver member.

4. The method of claim 1, wherein the torque limiter causes the driver to move from the first position to the second position when a torque applied to the driver exceeds the threshold torque.

5. The method of claim 4, wherein the torque limiter translates axially along a longitudinal axis of the first and second shafts when the driver moves between the first position and the second position.

6. The method of claim 1, wherein actuating the driver comprises activating an external power source to cause the driver to rotate.

7. The method of claim 1, wherein the torque limiter comprises a first engaging member and a second engaging member, wherein the first engaging member engages with a first complementary engaging member of the first shaft when the driver is in a first position, and the second engaging member engages with a second complementary engaging member of the second shaft when the driver is in the second position.

8. The method of claim 7, wherein the first engaging member is positioned in a first plane and the second engaging member is positioned in a second plane that is spaced a distance apart from the first plane.

9. The method of claim 7, wherein the first engaging member and the first complementary engaging member are positioned in the same plane when the driver is in the first position, and wherein the first engaging member and the first complementary engaging member are positioned in different planes when the driver is in the second position.

10. A method for operating a bone anchor driver, comprising:
    rotating a driver to simultaneously rotate a torque limiter and an outer shaft coupled to the driver to thereby drive a first closure mechanism onto a bone anchor, wherein the driver decouples from the outer shaft when a torque being applied to the driver exceeds a first predetermined threshold torque;
    continuing to rotate the driver while the driver is decoupled from the outer shaft to cause the torque limiter to rotate relative to the outer shaft and engage an inner shaft on the driver to thereby couple the driver to the inner shaft; and
    continuing to rotate the driver while the driver is coupled to the inner shaft to simultaneously rotate the torque limiter and the inner shaft relative to the outer shaft to thereby drive a second closure mechanism into the bone anchor, wherein the driver decouples from the inner shaft when the torque being applied to the driver exceeds a second predetermined threshold torque.

11. The method of claim 10, wherein the second predetermined threshold torque is different than the first predetermined threshold.

12. The method of claim 10, wherein the second predetermined threshold torque is greater than the first predetermined threshold.

13. The method of claim 10, wherein driving the first closure mechanism onto the bone anchor locks a receiver member of the bone anchor in a fixed angular orientation with respect to a bone engaging member of the bone anchor, and driving the second closure mechanism into the bone anchor locks a spinal fixation element in a fixed position within the receiver member of the bone anchor.

14. The method of claim 10, wherein the torque limiter translates axially along a longitudinal axis of the outer and inner shafts when the driver disengages the outer shaft and engages the inner shaft.

15. The method of claim 10, wherein actuating the driver comprises activating an external power source to cause the driver to rotate.

16. A method for operating a bone anchor driver, comprising:
    providing a bone anchor driver, the bone anchor driver including
       a rotatable actuator,
       a torque limiting mechanism coupled to the actuator such that rotation of the actuator causes corresponding rotation of the torque limiting mechanism,
       an outer shaft having the torque limiting mechanism fully disposed therein, the outer shaft being configured to engage an outer closure mechanism coupled to a bone anchor assembly, and
       an inner shaft disposed within the torque limiting mechanism, the inner shaft being configured to engage an inner closure mechanism coupled to a bone anchor assembly;
    applying a first torque to the actuator to rotate the actuator and the torque limiting mechanism to thereby cause the torque limiting mechanism to engage and rotate the outer shaft relative to the inner shaft; and applying a second torque to the actuator to cause the torque limiting mechanism to automatically slide axially within the outer shaft and around the inner shaft to disengage from the outer shaft and engage the inner shaft to thereby cause rotation of the inner shaft relative to the outer shaft, wherein the second torque exceeds the first torque.

17. The method of claim 16, wherein the inner and outer shafts each includes ramps formed thereon for engaging with corresponding ramps formed on the torque limiting mechanism to cause axially sliding of the torque limiting mechanism.

18. The method of claim 16, wherein driving the first closure mechanism onto the bone anchor locks a receiver member of the bone anchor in a fixed angular orientation with respect to a bone engaging member of the bone anchor, and driving the second closure mechanism into the bone anchor locks a spinal fixation element in a fixed position within the receiver member of the bone anchor.

19. The method of claim 16, wherein actuating the driver comprises activating an external power source to cause the driver to rotate.

* * * * *